(12) United States Patent
Liu

(10) Patent No.: US 11,337,458 B2
(45) Date of Patent: May 24, 2022

(54) VAPORIZER HAVING MEANS FOR PAUSING VAPORIZING OF CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 212 days.

(21) Appl. No.: 16/680,462

(22) Filed: Nov. 11, 2019

(65) Prior Publication Data

US 2020/0359706 A1   Nov. 19, 2020

(30) Foreign Application Priority Data

May 13, 2019  (CN) .......................... 201910395453.1
May 13, 2019  (CN) .......................... 201920682807.6

(51) Int. Cl.
*A24F 13/00* (2006.01)
*A24F 17/00* (2006.01)
*A24F 25/00* (2006.01)
*A24F 40/40* (2020.01)
*A61M 11/04* (2006.01)

(52) U.S. Cl.
CPC ............ *A24F 40/40* (2020.01); *A61M 11/042* (2014.02)

(58) Field of Classification Search
CPC ........ A24F 40/20; A24F 40/40; A61M 11/042
See application file for complete search history.

(56) References Cited

U.S. PATENT DOCUMENTS

| 2012/0204889 A1* | 8/2012 | Xiu ........................ A24F 40/30 |
| | | 131/273 |
| 2014/0007891 A1* | 1/2014 | Liu ......................... A24F 40/40 |
| | | 131/329 |
| 2018/0213845 A1* | 8/2018 | Qiu ....................... A24F 40/485 |
| 2019/0133190 A1* | 5/2019 | Chen ...................... A24F 40/40 |
| 2019/0142069 A1* | 5/2019 | Qiu ....................... A24F 40/485 |
| | | 131/329 |
| 2020/0054074 A1* | 2/2020 | Xiaojun ................... A24F 9/16 |

FOREIGN PATENT DOCUMENTS

CN          109156862       *   1/2019   ............. A24F 40/40

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

A vaporizer including a first outer casing; a second outer casing; a main body; a turnover member; a first heating unit; a second heating unit; a first connector; a second connector; a fastener; a fixed part; a pneumatic switch; a buckle; a fixing pin; a first spring; a second spring; a button; a support frame; a control plate; a light column; a battery. The main body is disposed between the first outer casing and the second outer casing and includes a side wall and a through hole disposed in the side wall. The turnover member is disposed at one side of the main body and is next to the through hole of the main body. The first heating unit is cup-shaped and communicates with the through hole of the main body. The turnover member is curved and fixed on the main body via the buckle.

2 Claims, 3 Drawing Sheets

VAPORIZER HAVING MEANS FOR PAUSING VAPORIZING OF CIGARETTE

CROSS-REFERENCE TO RELATED APPLICATIONS

Pursuant to 35 U.S.C. § 119 and the Paris Convention Treaty, this application claims foreign priority to Chinese Patent Application No. 201910395453.1 filed May 13, 2019, and to Chinese Patent Application No. 201920682807.6 filed May 13, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a vaporizer.

A vaporizer, colloquially known as a vape, is a device used to vaporize substances such as tobacco for inhalation.

SUMMARY

The disclosure provides a vaporizer.

The vaporizer comprises a first outer casing; a second outer casing; a main body disposed between the first outer casing and the second outer casing, the main body comprising a side wall and a through hole disposed in the side wall; a turnover member disposed at one side of the main body and being next to the through hole of the main body; a first heating unit being cup-shaped and disposed under the through hole of the main body; a second heating unit; a first connector; a second connector; a fastener; a fixed part; a pneumatic switch; a buckle; a fixing pin; a first spring; a second spring; a button; a support frame; a control plate; a light column; a battery.

The turnover member is curved and fixed on the main body via the buckle and is capable of overturning outwards with respect to the main body; the first heating unit abuts against the turnover member; the second heating unit is disposed below the first heating unit and on the first connector; the first connector is sheathed on the second connector and fixed by the fastener; the pneumatic switch is disposed in the fixed part; the fixed part is disposed in the fastener; the second connector is disposed at an inner side of the turnover member; the first spring is disposed on the turnover member; the turnover member is fixed on the main body via the fixing pin; the main body comprises a groove; the button is disposed on the support frame, and the support frame is embedded in the groove; the second spring is disposed on the buckle; the control plate is disposed on the main body; the light column is fixed on the control plate; and the battery is disposed at one side of the main body and between the first outer casing and the second outer casing.

Advantages of the vaporizer according to embodiments of the disclosure are summarized as follows. The turnover member is disposed at one side of the main body and is next to the through hole of the main body. Press the buckle, the turnover member can be released from the buckle and ejects outwards with respect to the main body. Thus, the cigarette is released from the first heating unit, and the vaporizing of the cigarette is paused. Returning the turnover member on the buckle and inserting the cigarette, the vaporizing can be restarted. So, it is easy to control the start and pause of the vaporizing.

The vaporizer comprises a first heating unit and the second heating unit, and the side and the bottom of the cigarette can be synchronously heated by the first heating unit and the second heating unit, respectively, which can accelerate the volatilization degradation of harmful substances in the cigarette.

DETAILED DESCRIPTION

Figure 1:
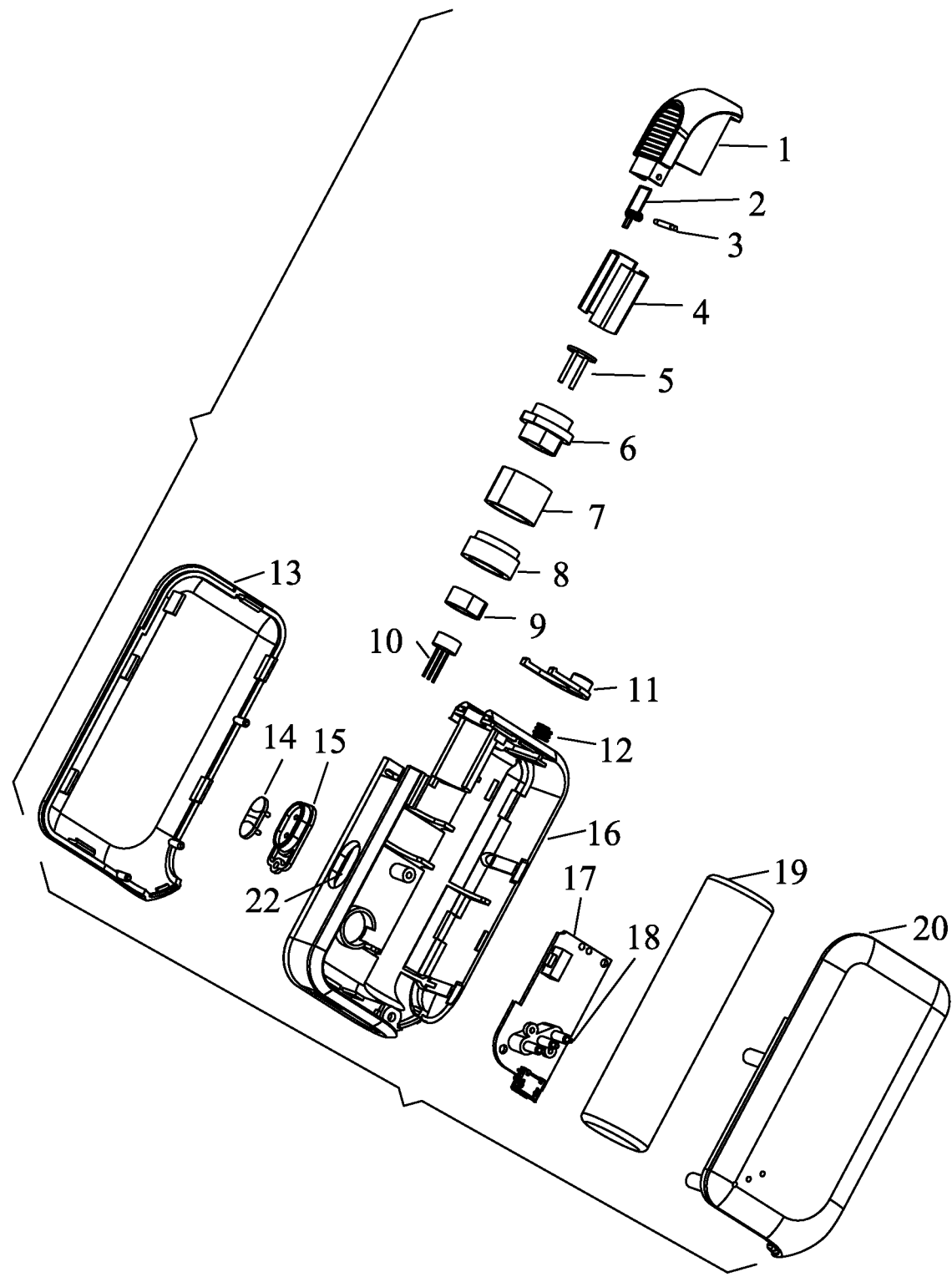
FIG. 1 is an exploded view of a vaporizer according to one embodiment of the disclosure.
Figure 2:
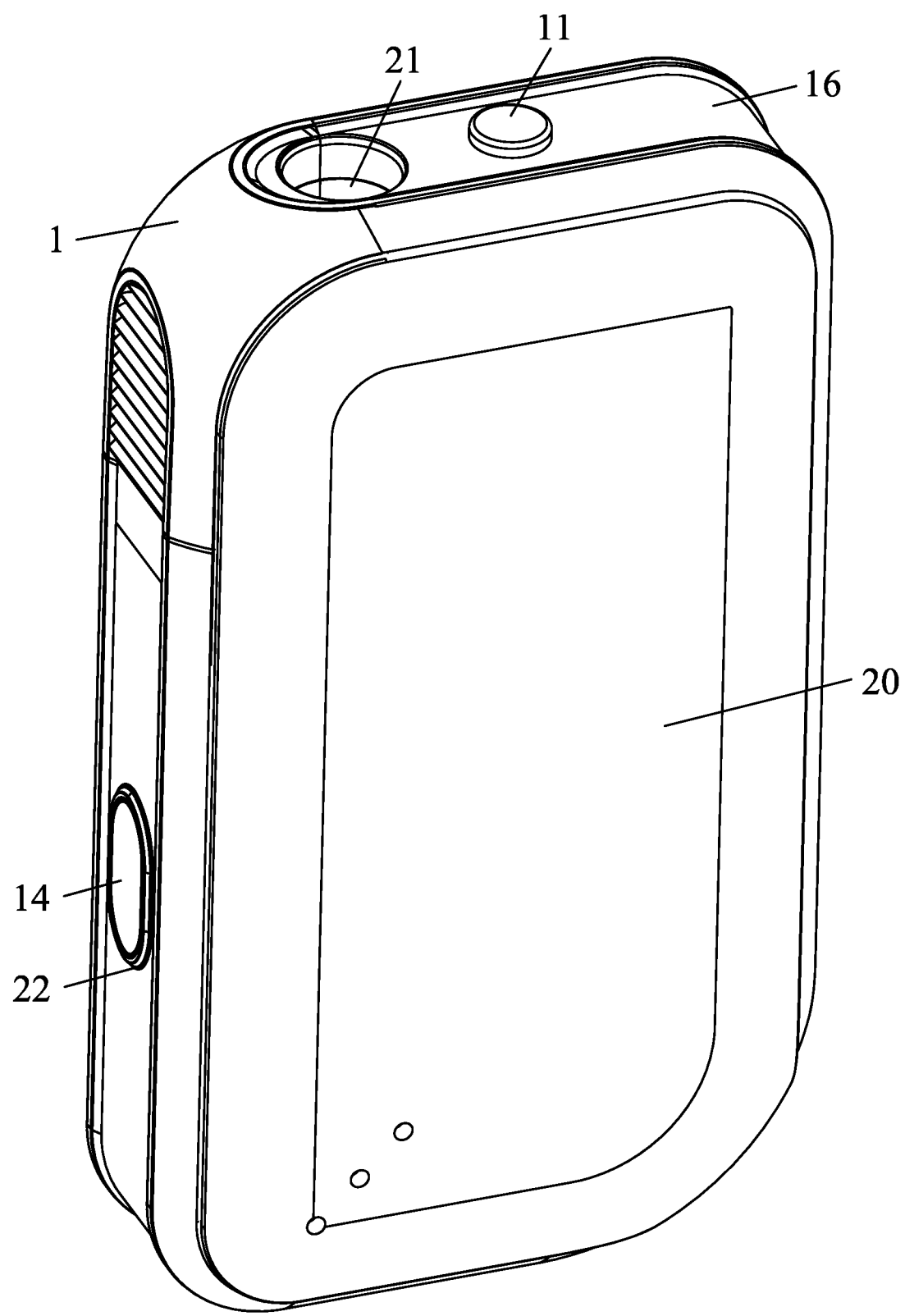
FIG. 2 is a schematic diagram of a vaporizer according to one embodiment of the disclosure.
Figure 3:
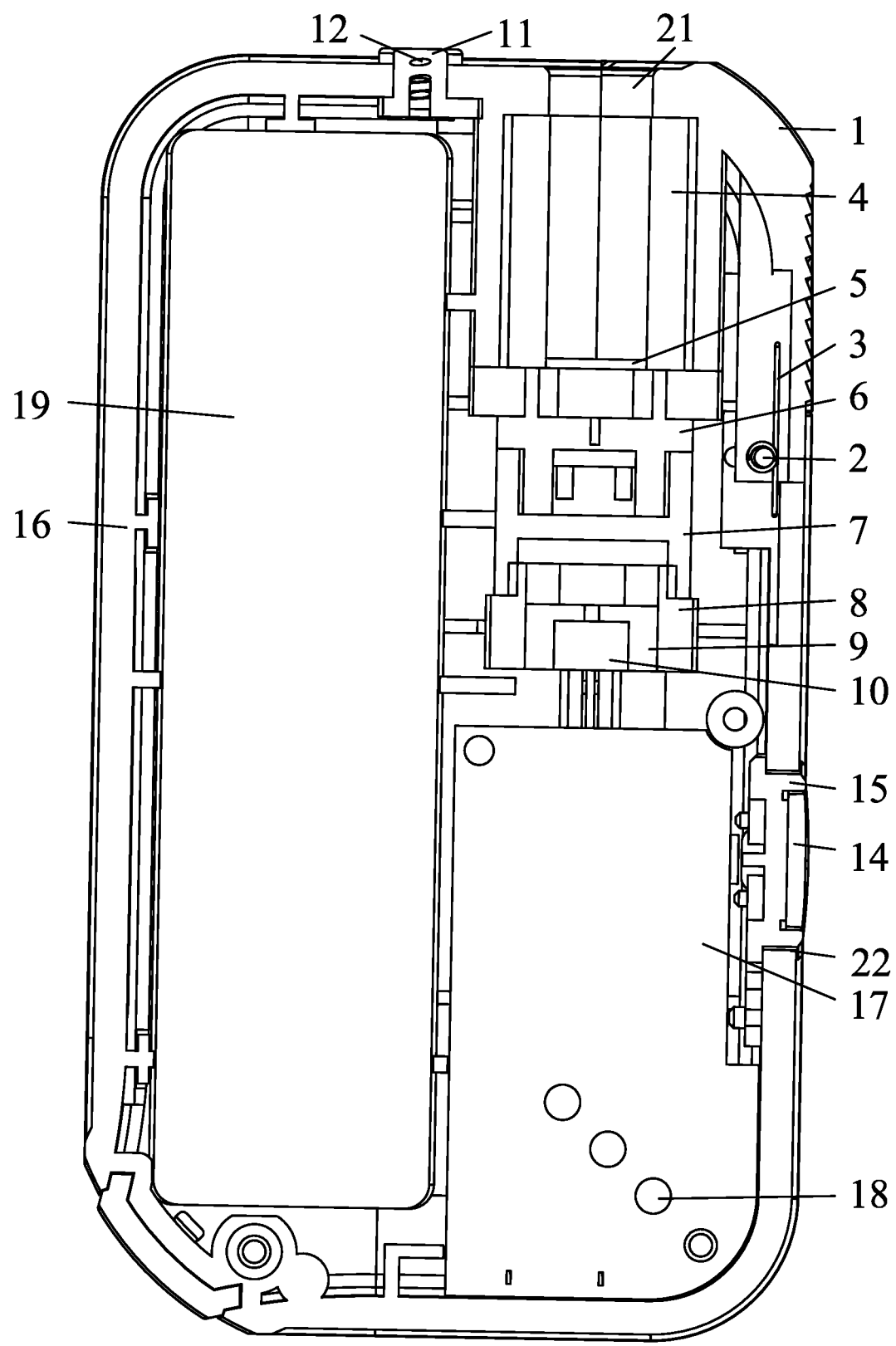
FIG. 3 is a sectional view of a vaporizer according to one embodiment of the disclosure.

To further illustrate, embodiments detailing a vaporizer are described below. It should be noted that the following embodiments are intended to describe and not to limit the disclosure.

A vaporizer comprises a first outer casing 13; a second outer casing 20; a main body 16; a turnover member 1; a first heating unit 4; a second heating unit 5; a first connector 6; a second connector 7; a fastener 8; a fixed part 9; a pneumatic switch 10; a buckle 11; a fixing pin 3; a first spring 2; a second spring 12; a button 14; a support frame 15; a control plate 17; a light column 18; a battery 19. The main body 16 is disposed between the first outer casing 13 and the second outer casing 20 and comprises a side wall and a through hole 21 disposed in the side wall. The turnover member 1 is disposed at one side of the main body 16 and is next to the through hole 21 of the main body 16. The first heating unit 4 is cup-shaped and communicates with the through hole 21 of the main body 16.

The turnover member 1 is curved and fixed on the main body 16 via the buckle 11 and is capable of overturning outwards with respect to the main body; the first heating unit 4 abuts against the turnover member 1; the second heating unit 5 is disposed below the first heating unit 4 and on the first connector 6; the first connector 6 is sheathed on the second connector 7 and fixed by the fastener 8; the pneumatic switch 10 is disposed in the fixed part 9; the fixed part 9 is disposed in the fastener 8; the second connector 7 is disposed at an inner side of the turnover member 1; the first spring 2 is disposed on the turnover member 1; the turnover member 1 is fixed on the main body 16 via the fixing pin 3; the main body 16 comprises a groove 22; the button 14 is disposed on the support frame 15, and the support frame 15 is embedded in the groove 22; the second spring 12 is disposed on the buckle 11; the control plate 17 is disposed on the main body 16; the light column 18 is fixed on the control plate 17; and the battery 19 is disposed at one side of the main body 16 and between the first outer casing 13 and the second outer casing 20.

In use, the cigarette is inserted in the first heating unit 4 from the through hole 21 of the main body 16. The turnover member 1 is fixed on the main body 16 via the buckle 11 and is next to the through hole 21 of the main body. Press the buckle 11, the turnover member 1 can be released from the buckle, and under the action of the first spring 2, the turnover member 1 ejects outwards with respect to the main body 16, and the cigarette is also released from the first heating unit 4. Thus, the vaporizing of the cigarette is paused. Return the turnover member 1 on the buckle 11 to lock the turnover member 1 on the main body 16, and press the button 14, the vaporizing can be restarted. So, it is easy to control the start and pause of the vaporizing.

Pressing the button 14 can power on the vaporizer, and the first heating unit 4 starts to work and vaporize the cigarette. In the process of inhaling, the vapor drives the pneumatic switch 10 to work, and the second heating unit 5 starts to vaporize the cigarette. Thus, both the side and the bottom of the cigarette are heated, which can accelerate the volatilization degradation of harmful substances in the cigarette.

It will be obvious to those skilled in the art that changes and modifications may be made, and therefore, the aim in the appended claims is to cover all such changes and modifications.

What is claimed is:

1. A device, comprising:
   1) a first outer casing;
   2) a second outer casing;
   3) a main body disposed between the first outer casing and the second outer casing, the main body comprising a side wall and a through hole disposed in the side wall;
   4) a turnover member disposed at one side of the main body and being next to the through hole of the main body;
   5) a first heating unit being cup-shaped and disposed under the through hole of the main body;
   6) a second heating unit;
   7) a first connector;
   8) a second connector;
   9) a fastener;
   10) a fixed part;
   11) a pneumatic switch;
   12) a buckle;
   13) a fixing pin;
   14) a first spring;
   15) a second spring;
   16) a button;
   17) a support frame;
   18) a control plate;
   19) a light column; and
   20) a battery;

wherein:
   the through hole is adapted for inserting a cigarette into the first heating unit;
   the turnover member is curved and fixed on the main body via the buckle and is capable of overturning outwards with respect to the main body;
   the first heating unit abuts against the turnover member; the second heating unit is disposed below the first heating unit and on the first connector; the first connector is sheathed on the second connector and fixed by the fastener;
   the pneumatic switch is disposed in the fixed part; the fixed part is disposed in the fastener; the second connector is disposed at an inner side of the turnover member; the first spring is disposed on the turnover member; the turnover member is fixed on the main body via the fixing pin;
   when the buckle is not pressed, the turnover member is locked by the buckle;
   when the buckle is pressed, the turnover member is released from the buckle and is ejected outward with respect to the main body under the action of the first spring so as to draw the cigarette out from the first heating unit;
   the main body comprises a groove; the button is disposed on the support frame, and the support frame is embedded in the groove; the second spring is disposed on the buckle;
   the control plate is disposed on the main body; the light column is fixed on the control plate; and
   the battery is disposed at one side of the main body and between the first outer casing and the second outer casing.

2. The device of claim 1, wherein when the turnover member is ejected outward with respect to the main body and the cigarette is drawn out from the first heating unit, the vaporizing of the cigarette is paused.

* * * * *